(12) United States Patent
Maguin et al.

(10) Patent No.: US 9,897,477 B2
(45) Date of Patent: Feb. 20, 2018

(54) DELIVERY UNIT WITH FILL LEVEL SENSOR FOR A LIQUID ADDITIVE, TANK FOR STORING LIQUID ADDITIVE, MOTOR VEHICLE AND METHOD FOR MONITORING A FILL LEVEL

(71) Applicant: EMITEC GESELLSCHAFT FUER EMISSIONSTECHNOLOGIE MBH, Lohmar (DE)

(72) Inventors: Georges Maguin, Marly (FR); Cheikh Diouf, Silly-sur-Nied (FR); Sven Schepers, Troisdorf (DE); Jan Hodgson, Troisdorf (DE)

(73) Assignee: EMITEC Gesellschaft fuer Emissionstechnologie mbH, Lohmar (DE)

( * ) Notice: Subject to any disclaimer, the term of this patent is extended or adjusted under 35 U.S.C. 154(b) by 627 days.

(21) Appl. No.: 14/487,304

(22) Filed: Sep. 16, 2014

(65) Prior Publication Data
US 2015/0000396 A1  Jan. 1, 2015

Related U.S. Application Data

(63) Continuation of application No. PCT/EP2013/053976, filed on Feb. 27, 2013.

(30) Foreign Application Priority Data
Mar. 16, 2012 (DE) .......... 10 2012 005 281

(51) Int. Cl.
G01F 23/296 (2006.01)
F01N 3/20 (2006.01)
(Continued)

(52) U.S. Cl.
CPC .......... *G01F 23/2962* (2013.01); *F01N 3/20* (2013.01); *F01N 3/2066* (2013.01);
(Continued)

(58) Field of Classification Search
CPC ............ G01F 23/2962; G01F 23/2968; G01F 25/0061; G01F 23/296; G01F 23/2961;
(Continued)

(56) References Cited

U.S. PATENT DOCUMENTS 2,869,108 A * 1/1959 Smith, Jr. ............... G01S 7/003
114/126
3,214,974 A * 11/1965 Altman ................. G01F 23/296
367/151
(Continued)

FOREIGN PATENT DOCUMENTS

CN 1894563 A 1/2007
CN 101458113 A 6/2009
(Continued)

*Primary Examiner* — Peter Macchiarolo
*Assistant Examiner* — David L Singer
(74) *Attorney, Agent, or Firm* — Laurence A. Greenberg; Werner H. Stemer; Ralph E. Locher

(57) ABSTRACT

A delivery unit for extracting liquid additive from a tank can be mounted on the tank and includes a fill level sensor for measuring the fill level of liquid additive in the tank. The fill level sensor is set up to emit waves into an emission region of the tank, and the fill level can be measured by using a propagation time measurement of the waves reflected by a liquid surface and striking the fill level sensor again. At least one first reference surface extends at least partially into the emission region and is at a first distance from the fill level sensor. The at least one first reference surface is disposed on a separate calibration component mounted on an outer side (Continued)

of a housing of the delivery unit. A tank for storing liquid additive, a motor vehicle and a method for monitoring a fill level are also provided.

13 Claims, 3 Drawing Sheets

(51) Int. Cl.
*G01F 25/00* (2006.01)
*G01N 25/00* (2006.01)

(52) U.S. Cl.
CPC ......... *G01F 25/0061* (2013.01); *G01N 25/00* (2013.01); *F01N 2560/12* (2013.01); *F01N 2610/02* (2013.01); *F01N 2610/1406* (2013.01); *F01N 2610/148* (2013.01); *F01N 2900/1811* (2013.01); *F01N 2900/1814* (2013.01); *Y02T 10/24* (2013.01)

(58) Field of Classification Search
CPC .... G01F 23/28; G01F 23/282–23/2928; Y10S 367/908; G01N 2291/045; G01S 2007/52014; F01N 2560/12; F01N 2610/148; F01N 2900/1814
USPC ........... 73/292, 290 V, 61.49, 152.51, 290 R, 73/291, 597; 181/124; 367/99, 100, 908, 367/151; 702/55, 159; 340/621; 220/4.14
See application file for complete search history.

(56) References Cited

U.S. PATENT DOCUMENTS

| | | | |
|---|---|---|---|
| 3,884,074 A | | 5/1975 | Robertson |
| 3,985,030 A | | 10/1976 | Charlton |
| 4,229,798 A | * | 10/1980 | Rosie ................ G01F 23/2962 340/621 |
| 4,748,846 A | * | 6/1988 | Haynes ............... G01F 23/2962 73/290 V |
| 5,085,077 A | | 2/1992 | Stapleton et al. |
| 5,095,748 A | * | 3/1992 | Gregory ............. G01F 23/2961 702/54 |
| 5,301,549 A | * | 4/1994 | Sinclair ............... G01F 23/2961 340/621 |
| 5,309,763 A | * | 5/1994 | Sinclair ............... G01F 23/2961 181/124 |
| 5,357,801 A | * | 10/1994 | Sinclair ............... G01F 23/2962 181/124 |
| 5,568,449 A | * | 10/1996 | Rountree ............ G01F 23/2962 367/902 |
| 5,670,710 A | | 9/1997 | Atkinson |
| 5,765,433 A | * | 6/1998 | Johnson .................. G01F 17/00 73/290 V |
| 5,856,953 A | * | 1/1999 | Durkee ............... G01F 23/2962 367/908 |
| 6,151,956 A | * | 11/2000 | Takahashi ........... G01N 29/024 73/10 |
| 8,943,812 B2 | | 2/2015 | Schepers et al. |
| 2003/0155538 A1 | * | 8/2003 | Siepmann ........... G01F 23/2927 250/577 |
| 2004/0007061 A1 | * | 1/2004 | Forgue ................ G01F 23/2968 73/290 V |
| 2005/0150291 A1 | * | 7/2005 | Voss .................... G01F 23/2962 73/290 V |
| 2007/0203668 A1 | * | 8/2007 | Reimer ............... G01F 25/0061 702/159 |
| 2008/0098817 A1 | | 5/2008 | Jones |
| 2009/0282911 A1 | | 12/2009 | Bostroem |
| 2010/0010750 A1 | * | 1/2010 | Baron .................. G01L 9/0001 702/30 |
| 2010/0207807 A1 | * | 8/2010 | Kuhlow ................ G01F 23/284 342/124 |
| 2011/0301883 A1 | | 12/2011 | Murphy |
| 2012/0225396 A1 | | 9/2012 | Harr et al. |
| 2012/0311999 A1 | | 12/2012 | Hodgson et al. |
| 2013/0074590 A1 | | 3/2013 | Bertow et al. |
| 2014/0366512 A1 | | 12/2014 | Hodgson et al. |

FOREIGN PATENT DOCUMENTS

| | | | | |
|---|---|---|---|---|
| DE | 3706453 A1 | * | 9/1988 | ........... G01F 23/292 |
| DE | 19637978 A1 | | 4/1997 | |
| DE | 102004028547 A1 | | 2/2006 | |
| DE | 102009041938 A1 | | 3/2011 | |
| DE | 102009055738 A1 | | 6/2011 | |
| DE | 102010004614 A1 | * | 7/2011 | ........... F01N 3/2066 |
| DE | 102010035008 A1 | | 2/2012 | |
| EP | 2341224 A1 | | 7/2011 | |
| JP | H06174531 A | | 6/1994 | |
| JP | 2001208595 A | | 8/2001 | |
| JP | 2010054221 A | | 3/2010 | |
| KR | 1020030054419 A | | 7/2003 | |
| KR | 1020080048825 A | | 6/2008 | |
| WO | 2011085830 A1 | | 7/2011 | |
| WO | WO 2012123344 A1 | * | 9/2012 | ........... G01F 23/296 |
| WO | 2013127804 A1 | | 9/2013 | |

* cited by examiner

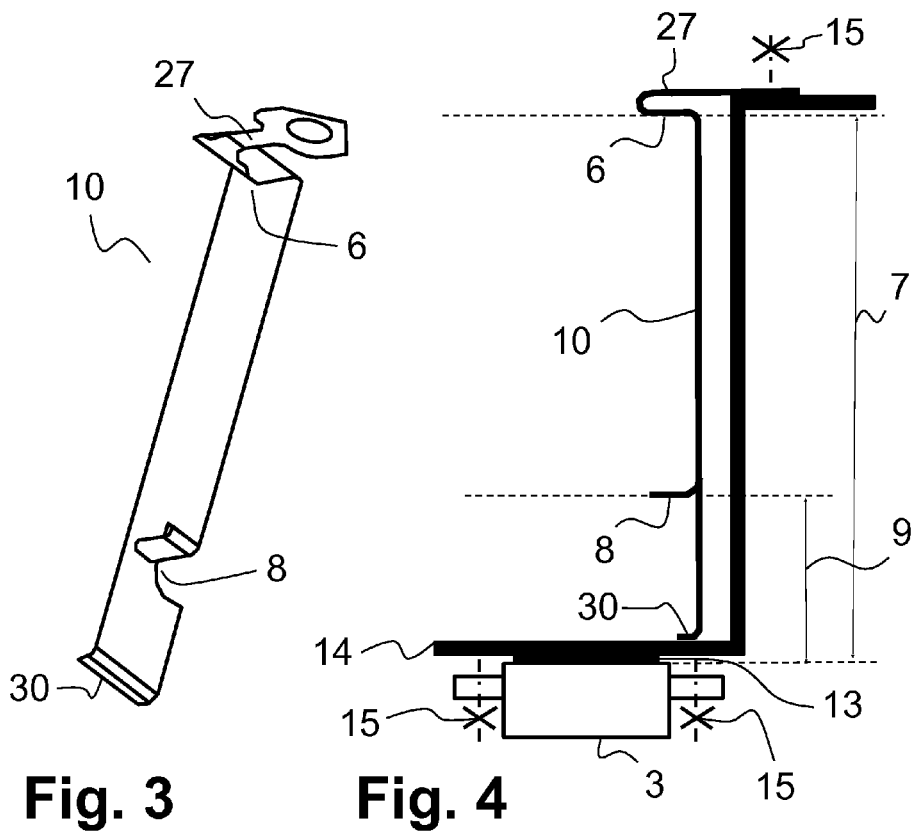
Fig. 3  Fig. 4
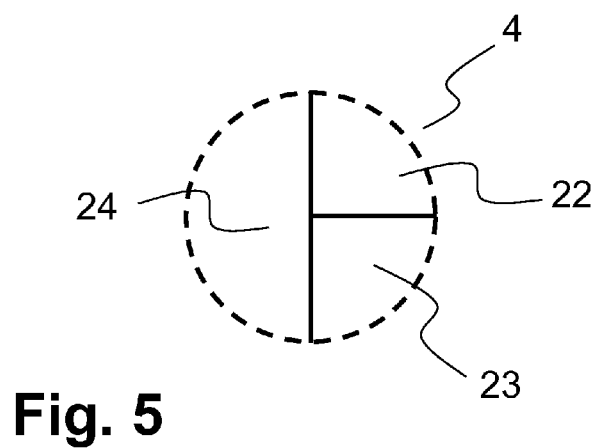
Fig. 5

DELIVERY UNIT WITH FILL LEVEL SENSOR FOR A LIQUID ADDITIVE, TANK FOR STORING LIQUID ADDITIVE, MOTOR VEHICLE AND METHOD FOR MONITORING A FILL LEVEL

CROSS-REFERENCE TO RELATED APPLICATION

This is a continuation, under 35 U.S.C. § 120, of copending International Application No. PCT/EP2013/053976, filed Feb. 27, 2013, which designated the United States; this application also claims the priority, under 35 U.S.C. § 119, of German Patent Application DE 10 2012 005 281.2, filed Mar. 16, 2012; the prior applications are herewith incorporated by reference in their entirety.

BACKGROUND OF THE INVENTION

Field of the Invention

The invention relates to a delivery unit for extracting liquid additive from a tank. The delivery unit includes a sensor for determining the fill level in the tank. The delivery unit is suitable, in particular, for delivering liquid additive from a tank into an exhaust-gas treatment device, for the purification of exhaust gases of an internal combustion engine, in a motor vehicle. The invention also relates to a tank for storing liquid additive, a motor vehicle and a method for monitoring a fill level.

In particular, in the field of mobile internal combustion engines for motor vehicles, exhaust-gas treatment devices are often used to implement exhaust-gas purification methods in which the exhaust gases of the internal combustion engine are purified with the aid of a liquid additive. An exhaust-gas purification method which is particularly commonly used in such exhaust-gas treatment devices is the selective catalytic reduction (SCR) method in which nitrogen oxide compounds in the exhaust gas of the internal combustion engine are reduced with the aid of a reducing agent. In this context, ammonia is commonly used as the reducing agent. Ammonia is generally not stored directly in pure form in the motor vehicle but rather is stored in the form of a reducing agent precursor solution which is converted in the exhaust gas, or in a reactor provided specifically for that purpose, to form ammonia. The reducing agent precursor solution then constitutes the liquid additive. A particularly commonly used reducing agent precursor solution is aqueous urea-water solution, which is available, for example, under the trademark AdBlue® and has a urea content of 32.5%. The expressions "reducing agent" and "reducing agent precursor solution" will hereinafter be used synonymously for one another, and are both encompassed by the expression "additive."

In order to provide the reducing agent in an exhaust-gas treatment device, a delivery unit is generally provided which delivers the reducing agent from a tank to the exhaust-gas treatment device. Such a delivery unit should be constructed to be durable, as inexpensive as possible and as simple as possible with regard to assembly and servicing. Development has in the meantime led to delivery units which are installed in the tank for the reducing agent. In the case of such delivery units, it is generally possible to dispense with the connecting lines between the tank and the delivery unit. Such a delivery unit is known, for example, from International Publication No. WO 2011/085830 A1, corresponding to U.S. Patent Application Publication No. 2012/0311999.

A delivery unit of that type is particularly advantageous if it additionally has measures with which the fill level in the tank can be monitored. It is a problem in that case that the delivery unit should as far as possible be constructed to be installed in different tanks, and that the measurement of the fill level should be as independent as possible of the shape/height of the tank.

SUMMARY OF THE INVENTION

It is accordingly an object of the invention to provide a delivery unit with a fill level sensor for a liquid additive, a tank for storing liquid additive, a motor vehicle and a method for monitoring a fill level, which overcome the hereinafore-mentioned disadvantages and at least alleviate the highlighted technical problems of the heretofore-known units, vehicles and methods of this general type. It is sought, in particular, to propose an especially advantageous delivery unit for extracting liquid additive from a tank, in which the delivery unit has a particularly advantageous fill level sensor. Furthermore, it is sought to specify a particularly advantageous method for monitoring the fill level of a liquid additive in a tank.

With the foregoing and other objects in view there is provided, in accordance with the invention, a delivery unit for extracting liquid additive from a tank, in which the delivery unit may be mounted on the tank and has a fill level sensor for measuring the fill level of liquid additive in the tank. The fill level sensor is constructed to emit waves into an emission region of the tank, in such a way that the fill level can be measured by using a propagation time measurement of the waves that are reflected by a liquid surface and strike the fill level sensor again. In this case, the delivery unit has at least a first reference surface which extends at least partially into the emission region and is at a first distance from the fill level sensor, and the at least one first reference surface is disposed on a separate calibration component which is mounted on an outer side of a housing of the delivery unit.

The delivery unit is preferably formed with a housing in which the various active components of the delivery unit are situated. The active components are, for example, a valve, a pump for delivering the liquid additive, a sensor or the like. The delivery unit can preferably be inserted with its housing into a (base) opening of the tank base. For this purpose, the delivery unit preferably has a flange constructed to produce a fluid-tight connection between the delivery unit and the tank. The delivery unit or the housing thereof then preferably extends into the interior of the tank proceeding from the tank base. The delivery unit preferably has a suction point which is situated in the interior of the tank when the delivery unit is mounted on the tank and through which the delivery unit can suck liquid additive out of the interior of the tank. A discharge point at which liquid additive can be discharged is preferably also provided on the delivery unit. The discharge point is constructed, for example, as a port to which a line can be connected through which the liquid additive can be conducted from the delivery unit to a feed device on an exhaust-gas treatment device.

The fill level sensor preferably has an emitter, which emits (optical, acoustic, electromagnetic or similar) waves into the emission region, and a receiver, which can receive the waves emitted by the fill level sensor. In this case, between being emitted and received, the waves may also be reflected by a suitable surface. The emission region is to be understood, in particular, to mean a spatial angle segment in which the fill level sensor emits waves. The emission region typically extends conically from the fill level sensor, in particular in the structural variant of an ultrasound sensor. The cone may, for example, have a cone opening angle of between 1° and 10° [degrees]. The emitter of the fill level sensor and the receiver of the fill level sensor are preferably coordinated with one another in such a way that the receiver receives (only) the waves emitted by the emitter or sender, and is preferably not adversely affected by disturbance signals from the environment. The waves emitted by the fill level sensor are preferably sound waves. It is, however, also possible for the sensor to emit and receive electromagnetic waves. The waves preferably have a frequency which is suitable for being (at least partially) (or totally) reflected by a surface of the liquid additive in the tank. It can thus be ensured that the waves are emitted from the fill level sensor to the liquid surface, are reflected there and diverted back to the fill level sensor. Accordingly, the time taken by the waves to travel from the fill level sensor to the liquid surface and back again is measured for the propagation time measurement. The fill level sensor is preferably aligned on the delivery unit in such a way that the emission region extends vertically upward (counter to gravity) proceeding from the fill level sensor when the delivery unit is mounted on a tank in an intended installation position. It can thus be ensured that the waves emitted by the fill level sensor strike a liquid surface of the additive in the tank at right angles and are reflected there vertically back to the fill level sensor.

It has been found that the propagation time in liquid additive may vary significantly because the speed of the waves in the liquid additive is affected by numerous cross-influences. A significant cross-influence is, for example, the composition of the liquid additive. The accuracy of the fill level measurement using such a fill level sensor which emits waves can be greatly increased if, in addition to the described propagation time measurement, a second propagation time measurement from the fill level sensor to a reference surface and back again is carried out. A reference measurement path then exists from the fill level sensor to the reference surface, over which reference measurement path the speed of the waves in the liquid additive is determined. The propagation time to the reference surface can then be compared with the propagation time to the liquid surface. In this way, a variation in the speed of the waves in the liquid additive and in the fill level measurement can be taken into consideration. Since the reference surface extends into the emission region of the fill level sensor, a part of the waves emitted by the fill level sensor into the emission region is reflected back to the fill level sensor by the reference surface. The first reference surface thus leads to an additional signal being picked up by the fill level sensor.

The first reference surface should be disposed in such a way that the first reference measurement path from the fill level sensor to the first reference surface lies below the liquid surface (if possible even in the case of a low fill level in the tank). The first reference surface is therefore preferably disposed at a relatively short first distance from the fill level sensor. The first reference surface is preferably disposed at a distance of less than 100 mm [millimeters], and the first distance is particularly preferably between 25 mm and 80 mm or even between 50 mm and 80 mm.

In accordance with another particularly advantageous feature of the delivery unit of the invention, the delivery unit has an additional second reference surface which likewise extends at least partially into the emission region and is at a second distance from the fill level sensor. An additional propagation time of the waves through the liquid additive can be determined by using a second reference surface of this type. The additional propagation time measurement may on one hand be used to provide an even more accurate reference for the correction of the propagation time measurement to the liquid surface. Furthermore, the additional propagation time measurement makes it possible to compare the propagation times over two known distances (from the fill level sensor to the two different reference surfaces and back), allowing further conclusions to be drawn regarding properties of the liquid additive. It is thus possible for a quality measurement of the liquid additive to be carried out by using the fill level sensor in parallel with the fill level measurement.

Furthermore, the second reference surface may also be utilized to compensate for manufacturing tolerances in the delivery unit. It is often the case that the first distance between the fill level sensor and the first reference surface and/or the second distance between the fill level sensor and the second reference surface are not known with particularly great accuracy, and/or the distances are subject to relatively large manufacturing tolerances. This may, for example, result from the fact that the fill level sensor is mounted on a plastic wall of the housing of the delivery unit, the form and thickness of which are subject to relatively large tolerances. It is, however, then nevertheless possible, if appropriate, for the distance between the first reference surface and the second reference surface to be adhered to with very high accuracy. The second reference surface is preferably at a second distance of 5 mm to 40 mm, particularly preferably 20 mm to 30 mm, from the fill level sensor. The first reference surface and the second reference surface are preferably at a distance of 30 mm to 60 mm from one another.

In accordance with a further advantageous feature of the delivery unit of the invention, the fill level sensor is an ultrasound sensor. An ultrasound sensor preferably emits and receives sound in a frequency range above the frequency range of audible sound. Typically, frequencies of greater than 16 kHz [16,000 1/second] are referred to as ultrasound. The ultrasound sensor preferably emits and receives sound waves in a frequency range of between 2 and 20 MHz [megahertz]. It has been found that particularly accurate propagation time measurements in liquid exhaust-gas additives and in particular in aqueous urea solution are possible using ultrasound. A particularly precise determination of the fill level in a tank for liquid additive and, in particular, in a tank for aqueous urea solution is therefore possible by using an ultrasound measurement.

The reference surfaces for the fill level measurement would often have to be positioned differently for different tank shapes. In the interests of inexpensive manufacturing of the delivery unit, it is however desirable for the delivery unit to be as far as possible of identical construction for different tanks. It is therefore particularly advantageous for the first (and/or also the second) reference surface to be formed on a single, relatively inexpensive component which can be easily adapted to different tanks and different applications of the delivery unit. The reference component can preferably also be retroactively mounted on and dismounted again from the delivery unit, in such a way that a delivery unit can also be adapted retroactively to different tanks and applications. The separate calibration component may, for example, be formed as a sheet-metal component. This offers the advantage that the distance between the reference surfaces can be adhered to particularly precisely in the case of a sheet-metal component of this type. The housing of the delivery unit is formed, for example, from plastic. In the case of the housing, it is under some circumstances not possible, or possible only with very high outlay, to adhere to particularly precise manufacturing tolerances, in such a way that the reference surfaces which would otherwise be mounted directly on the housing and therefore also produced from plastic would not maintain their distance very reliably in a manufacturing run. That would be highly disadvantageous for the high accuracy of the propagation time measurement. That is now prevented in this case by using a separate calibration component.

It is furthermore also advantageous for at least the first reference surface, preferably the first reference surface and the second reference surface, to be disposed in such a way that the distance between the fill level sensor and the reference surface and the distance between the reference surfaces have the least possible temperature dependency. Due to thermal expansion, the distances on a component vary as a function of a temperature. Even if these variations are relatively small, they can have an effect on the measurement using the described fill level sensor which leads to an erroneous fill level measurement. It can be achieved that the distance has particularly low temperature dependency if the component provided for connecting the reference surface has a low coefficient of thermal expansion. This is possible if the reference surfaces are provided on a separate calibration component. The calibration component preferably has a low coefficient of thermal expansion, specifically of at most 50 μm/mK (micrometers per meter and Kelvin). This can be achieved by virtue of the calibration component being produced from metal, for example. The coefficient of thermal expansion of the housing of the delivery unit is normally higher, for example greater than 100 μm/mK, because the housing is produced from plastic, for example.

The calibration component preferably has a portion which abuts against the housing in the vicinity of the fill level sensor and thus predefines a distance between the reference surfaces and the fill level sensor. The portion may be, for example, a press-on portion which is pressed against a housing of the delivery unit in the vicinity of the fill level sensor and thereby abuts firmly against the housing.

In accordance with an added feature of the delivery unit of the invention, the at least one first reference surface can be individually positioned on the calibration component in order to define the first distance of the first reference surface to the fill level sensor. The calibration component may, for example, be produced from a prefabricated component which can be deformed by using a simple shaping process in order to form the reference surfaces. It is, for example, also advantageous in this case for the separate calibration component to be a sheet-metal strip from which the first reference surface and/or the second reference surface can simply be bent out.

Preferably, the calibration component includes a press-on portion. The press-on portion is, in particular, a bearing portion. Preferably, this press-on portion is pressed against a part of the wall of a housing of the delivery unit close to the fill level sensor. For example, it may be pressed against the wall directly opposite to the fill level sensor. The close position relative to the fill level sensor enables the distance from the calibration component to the fill level sensor to be defined very precisely even in the case that fabrication tolerances of the wall and/or the housing are not very accurate. Preferably, the calibration component has a high rigidity and is manufactured very precisely with accurate fabrication tolerances. This can be ensured by using a metallic material for the calibration component, preferably stainless steel. In particular, the portion of the calibration component between the press-on portion and the reference surfaces has very accurate fabrication tolerances. For example, these fabrication tolerances are ten times more precise than the fabrication tolerances of the housing of the delivery unit. The accurate fabrication tolerances of the calibration component permit the distance from the fill level sensor to the reference surfaces to always be very exact. Furthermore, the calibration component has a spring portion. This spring portion can be used to press the press-on portion against the wall of a housing at a defined position, although the distance between different fastening devices for the calibration component is not exactly known. Fastening devices for the calibration component can be holes for screwing the calibration component to the housing, for example. The spring portion is preferably not placed between the press-on portion and the reference surfaces but at another position of the calibration component because otherwise the spring portion may distort so as to negatively influence the precise distance between the press-on portion and the reference surfaces.

In accordance with an additional advantageous feature of the delivery unit of the invention, the fill level sensor is disposed in the housing of the delivery unit and is in contact with a wall of the housing through a coupling layer, and the fill level sensor is constructed to emit and receive waves through the wall.

The housing is preferably formed from plastic. An ultrasound sensor can easily emit and receive waves through a thin wall of the housing. The fill level sensor can therefore be disposed within the housing of the delivery unit and need not be in direct contact with the liquid additive. In order to improve the transmission of the waves from the fill level sensor to the housing, the coupling layer may be provided which connects the fill level sensor to the housing. The coupling layer (or transmission material) may, for example, take the form of a gel and/or a paste that produces a connection, which conducts waves (such as, for example, sound waves) in a particularly effective manner, between the fill level sensor and the housing.

The fill level sensor is fastened to the wall of the housing in the interior of the housing preferably by at least one fastening device or fastener. In this case, the fill level sensor is preferably pressed/clamped against the wall by the fastening device. The coupling layer is preferably fixedly braced between the fill level sensor and the wall by the at least one fastening device in such a way that permanent contact is produced between the fill level sensor, the coupling layer and the wall.

In accordance with yet another advantageous feature of the delivery unit of the invention, a temperature sensor for measuring the temperature of the liquid additive in the tank is disposed on the fill level sensor. The temperature of the liquid additive has a partially significant cross-influence on the speed of the waves in the liquid additive. It is therefore advantageous to measure the temperature of the liquid additive in the direct vicinity of the fill level sensor (in particular ultrasound sensor). A fill level sensor is preferably used which forms, with the temperature sensor, a common (conjoint) component which can be inserted in one piece into the delivery unit during the assembly of the delivery unit.

In accordance with yet a further advantageous feature of the delivery unit of the invention, the housing has a protuberance, and the temperature sensor is disposed in the housing in the protuberance. The protuberance preferably extends into the interior of the tank proceeding from the housing. The protuberance is therefore washed around by and/or filled with liquid additive which is present in the tank. A temperature sensor which is situated in the protuberance is consequently in direct contact with the liquid additive and can therefore precisely determine the temperature of the liquid additive. The protuberance is preferably at least partially lined with a form of coupling medium which produces direct thermal contact between the wall of the housing and the temperature sensor, in such a way that the temperature sensor can particularly precisely determine the liquid additive temperature prevailing at the outside of the wall/the coupling medium.

In accordance with yet an added feature of the delivery unit of the invention, the delivery unit may be set up to additionally measure/determine at least one property of the liquid additive, wherein for this purpose, at least one measurement of the propagation time of waves to the first reference surface and back to the fill level sensor is used. The propagation time of sound waves in aqueous urea solution is, for example, highly dependent on the concentration of the urea in the solution. It is therefore particularly advantageous if the fill level sensor not only performs the fill level measurement but also monitors the concentration of the liquid additive in the tank.

With the objects of the invention in view, there is furthermore provided a tank for storing liquid additive, comprising a tank base on which a delivery unit as described herein according to the invention is disposed.

With the objects of the invention in view, there is also provided a motor vehicle comprising at least an internal combustion engine, an exhaust-gas treatment device for the purification of the exhaust gases of the internal combustion engine, a tank for storing a liquid additive, and a delivery unit described herein according to the invention, the delivery unit being constructed to extract liquid additive from the tank and deliver the liquid additive into the exhaust-gas treatment device.

With the objects of the invention in view, there is furthermore provided a method for monitoring the fill level of a liquid additive in a tank by using at least one fill level sensor. The method comprises at least the following steps:
a) emitting a wave-form signal into the tank by using the fill level sensor and activating a time measurement;
b) receiving at least one first signal, which is reflected by a first reference surface, by using the fill level sensor and determining a first signal propagation time;
c) receiving a second signal, which is reflected by a liquid surface, by using the fill level sensor and determining a second signal propagation time; and
d) calculating a fill level by a comparison of the first signal propagation time and the second signal propagation time.

The described method is preferably carried out in an electronic control unit or controller to which the fill level sensor is connected and which has a timing unit through the use of which the time measurement for determining the different signal propagation times can be carried out. As already indicated by the sequence of steps of the described method, the signal reflected by the first reference surface generally (for example when a fill level lies above a reserve level) reaches the fill level sensor before the second signal reflected by the liquid surface reaches the fill level sensor. This is because the first reference surface is preferably disposed at a shorter distance from the fill level sensor than the liquid surface.

The described method is furthermore preferably repeatedly carried out iteratively in the form of a loop. In this case, the fill level sensor generally emits a wave signal in step a) and then, in steps b) and c), awaits the reflections of the signal from the first reference surface and from the liquid surface. The calculation of the fill level then takes place in step d). Step a) is subsequently carried out again. If appropriate, there may be a pause for a time interval before step a) is carried out again, in such a way that the described method should be carried out, for example, at least every 5 minutes, preferably at least every 15 minutes and particularly preferably at least every hour. If appropriate, the time interval may also vary (for example as a function of the determined fill level) or else be activated/changed in response to an external demand.

In accordance with a concomitant mode of the invention, the described method is particularly advantageous if, between step b) and step c), a further signal reflected by a second reference surface is received by the fill level sensor, and a further signal propagation time is determined, and wherein in a step e), at least one property of the liquid additive is determined by using a comparison of the first signal propagation time and the further signal propagation time. The receiving of the further reflected signal from the second reference surface preferably takes place in a step b.2) which lies temporally between step b) and step c).

A further propagation time measurement of waves in the liquid additive not only makes it possible to determine a property of the liquid additive. It is also possible for further cross-influences which may have an influence on the accuracy of the propagation time measurement used for the fill level measurement to be determined and minimized. For example, as a result of the fact that the fill level sensor is mounted in the housing of a delivery unit, it may be the case that the propagation time of the waves from the fill level sensor through the wall and, if appropriate, through a coupling layer into the liquid additive, differs depending on the installation situation. These manufacturing-induced differences may be compensated for by using a further propagation time measurement.

It should be noted in conjunction with the invention that the particular advantages and embodiment features specified with regard to the described delivery unit can be correspondingly applied and transferred to the described method. The same applies to the particular advantages and embodiment features specified with regard to the described method, which can likewise be applied and transferred to the delivery unit.

Other features which are considered as characteristic for the invention are set forth in the appended claims, noting that the features specified individually in the claims may be combined with one another in any desired technologically meaningful way and may be supplemented by explanatory facts from the description, with further structural variants of the invention being specified.

Although the invention is illustrated and described herein as embodied in a delivery unit with a fill level sensor for a liquid additive, a tank for storing liquid additive, a motor vehicle and a method for monitoring a fill level, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 3 is a perspective view of a calibration component for a delivery unit;

FIG. 4 is a fragmentary, elevational view of a portion of a delivery unit having a calibration component;

FIG. 5 is a diagram illustrating an emission region of a fill level sensor;

DETAILED DESCRIPTION OF THE INVENTION

Figure 1:
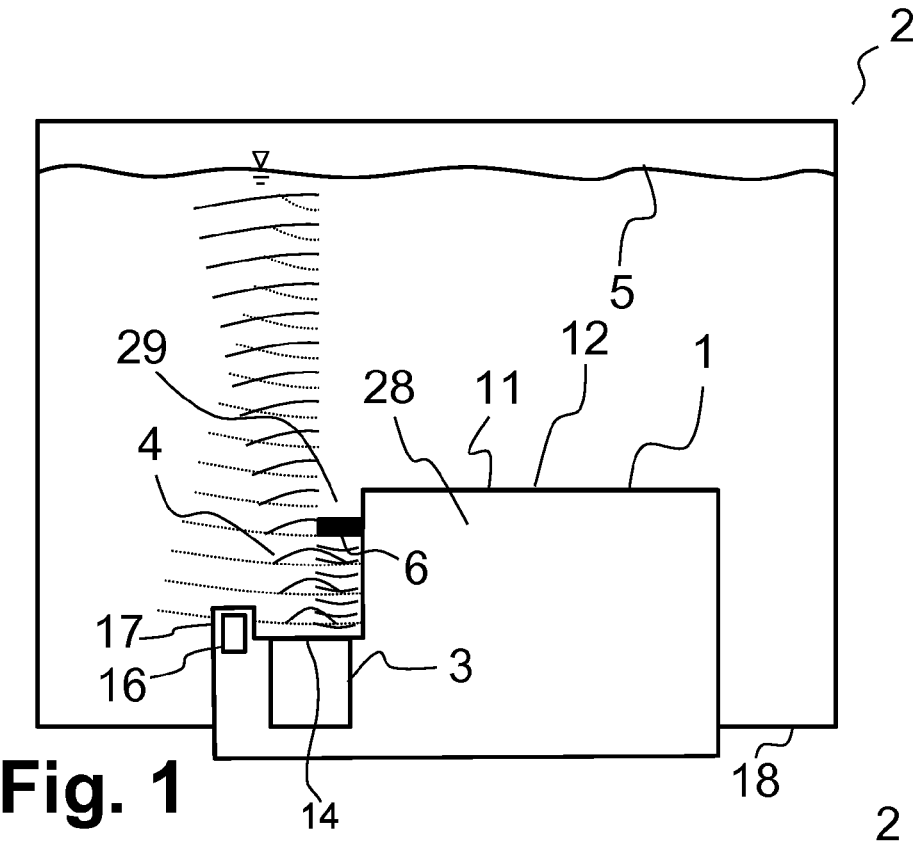
FIG. 1 is a diagrammatic, vertical-sectional view of a tank having a first structural variant of a delivery unit.
Figure 2:
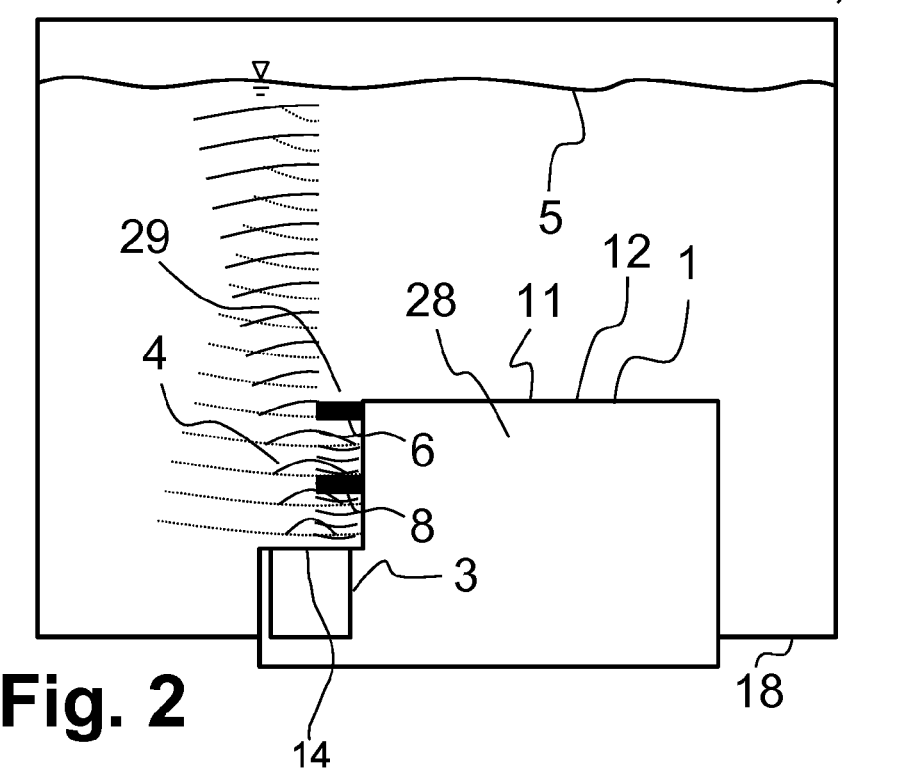
FIG. 2 is a vertical-sectional view of a tank having a second structural variant of a delivery unit.

Referring now in detail to the figures of the drawings, in which identical components are denoted by the same reference numerals and in which common features are explained jointly in part, and first, particularly, to FIGS. 1 and 2 thereof, there is seen in each case a tank 2. A delivery unit 1 is inserted into a tank base 18 of the tank 2. The delivery unit 1 has a fill level sensor 3 (ultrasound sensor) constructed to emit waves (or sound waves) into an emission region 4 in the tank 2. The waves are reflected by a liquid surface 5 of the liquid additive (urea-water solution) in the tank 2 and deflected back to the fill level sensor 3. In this way, the fill level sensor 3 can determine the distance between the liquid surface 5 and the fill level sensor 3, and thus the fill level of liquid additive in the tank 2, by using a propagation time measurement. The fill level sensor 3 is preferably disposed in an interior 28 of a housing 12 of the delivery unit 1. A wall 14 of the housing 12 thereby separates the fill level sensor 3 from the tank 2. The fill level sensor 3 is thereby protected from the liquid additive. The liquid additive is present in each case only on the outer side 11 of the housing 12 and does not pass into the interior 28.

According to FIGS. 1 and 2, in each case a first reference surface 6 is provided on the delivery unit 1. The first reference surface 6 extends into the emission region 4 and likewise leads to a reflection of waves which are emitted by the fill level sensor 3 into the tank 2. The waves reflected by the first reference surface 6 also travel back to the fill level sensor 3, in such a way that a propagation time measurement of waves from the fill level sensor 3 to the first reference surface 6 and back can be carried out. The first reference surface 6 causes a shielded region 29 to exist in the emission region 4. The waves emitted by the fill level sensor 3 do not pass into this shielded region 29 despite the fact that the shielded region would in fact lie in the emission region 4. The first reference surface 6 is constructed in such a way that the emission region 4 is not completely shielded by the first reference surface 6, and despite the first reference surface 6 a part of the waves emitted by the fill level sensor 3 can still travel to the liquid surface 5 and be reflected there.

According to FIG. 1, in addition to the fill level sensor 3, a temperature sensor 16 is situated in a protuberance 17 of the housing 12 of the delivery unit 1. The temperature sensor 16 and the fill level sensor 3 may also be formed as a common component.

In FIG. 2, in addition to the first reference surface 6, there is also provided a second reference surface 8 which likewise reflects waves emitted by the fill level sensor 3, in such a way that a propagation time measurement of waves to the second reference surface 8 and back to the fill level sensor 3 is also possible. In this case, the first reference surface 6 and the second reference surface 8 are not disposed directly one above the other, so that waves from the fill level sensor 3 strike both the first reference surface 6 and also the second reference surface 8, and two separate propagation time measurements are possible.

FIG. 3 illustrates a calibration component 10 which can be fastened to a housing of a delivery unit. The calibration component 10 forms a first reference surface 6 and a second reference surface 8. The calibration component is formed as a type of strip which is preferably composed of (a suitable metallic) sheet. In this way, it is possible to adhere particularly precisely to manufacturing tolerances with regard to the position of the first reference surface 6, of the second reference surface 8 and/or of a press-on portion 30 which is constructed for abutment in the vicinity of the fill level sensor 3. In order to ensure that the press-on portion 30 abuts precisely against a wall of the housing of a delivery unit, a spring portion 27 is provided in an upper region of the calibration component 10. The spring portion 27 deflects and ensures that the distance between the fill level sensor 3 and the first reference surface 6 and the second reference surface 8 is precisely adhered to even in the case of different heights of the housing of a delivery unit.

FIG. 4 shows a portion of a delivery unit having a calibration component 10. It is possible to see the wall 14 of the housing of the delivery unit. The fill level sensor 3 is mounted on the wall 14 in an interior 28 of the housing. The fill level sensor 3 is, for example, screwed or clamped to the wall 14 by a fastening device or fastener 15. A coupling layer 13 which is situated between the fill level sensor 3 and the wall 14 permits effective transmission of waves from the fill level sensor 3 to the wall and therefore to the outer side 11 and into the liquid additive in the tank. The calibration component 10 is mounted on the outer side 11 of the housing. The press-on portion 30 serves to ensure precise positioning of the calibration component 10 relative to the fill level sensor 3. It is possible to see the first reference surface 6, which is situated on the calibration component 10, at a first distance 7 from the fill level sensor 3. It is also possible to see the second reference surface 8, which is situated at a second distance 9 from the fill level sensor 3. The calibration component 10 is fastened to the wall 14 of the housing by the fastening device 15. The spring portion 27 serves to ensure that the press-on portion 30 of the calibration component 10 abuts against the wall 14 of the housing in the vicinity of the fill level sensor 3.

FIG. 5 shows a schematic illustration of the emission region 4 of a fill level sensor. In FIG. 5, the fill level sensor is viewed from above. Waves emitted by the fill level sensor in a first sector 22 preferably strike a first reference surface. Waves emitted by the fill level sensor in a second sector 23 preferably strike a second reference surface. Waves striking the reference surfaces are reflected back to the fill level sensor. In a third sector 24, waves emitted by the fill level sensor are not impeded by the reference surfaces but rather travel to a liquid surface of the additive in the tank, are reflected there and are transmitted back to the fill level sensor 3.

Figure 6:
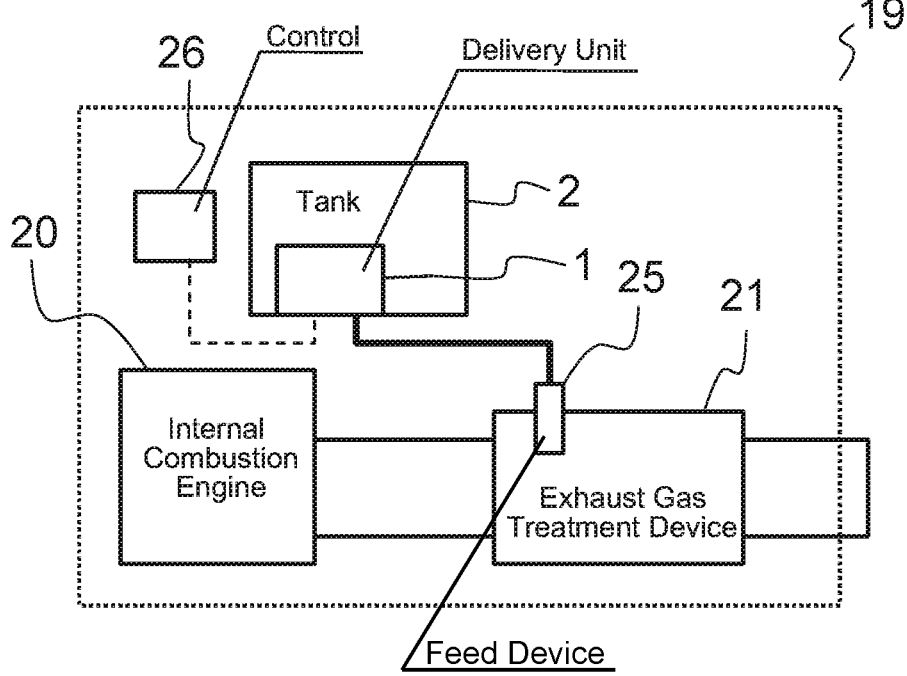
FIG. 6 is a block diagram of a motor vehicle.

FIG. 6 shows a motor vehicle 19 having an internal combustion engine 20 and an exhaust-gas treatment device 21 for the purification of exhaust gases of the internal combustion engine 20. Liquid additive can be fed into the exhaust-gas treatment device 21 by using a feed device 25. The liquid additive is preferably reducing agent, and particularly preferably aqueous urea solution. Liquid additive is supplied to the feed device 25 from a tank 2 by a delivery unit 1. A control unit 26, which is additionally provided in the motor vehicle, is used to control the delivery unit and is used, for example, to carry out a fill level measurement process.

Figure 7:
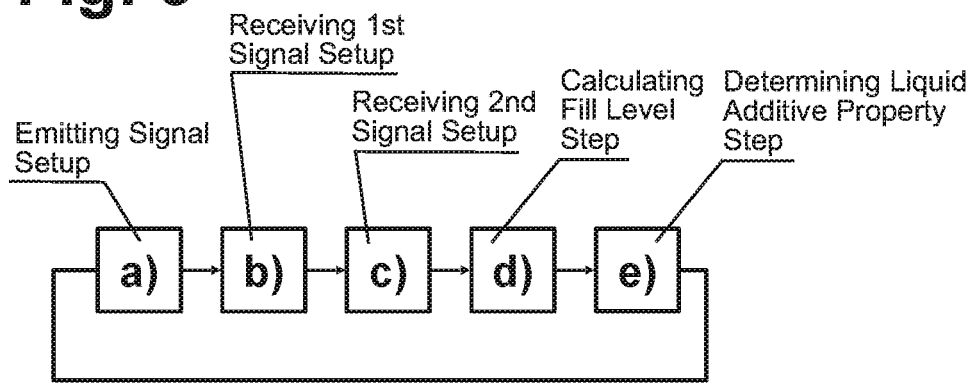
FIG. 7 is an embodiment of a flow diagram of a method for determining the fill level in the tank.

FIG. 7 shows the described method for fill level measurement in a flow diagram. It can be seen that method steps a) to e) are repeated in the form of a loop in order to attain up-to-date information regarding the fill level of liquid additive in the tank at regular intervals.

The features shown in the figures are generally not imperatively linked to one another, but rather may also be combined with embodiments from other figures. Likewise, the features of the structural variants shown in the figures may be considered individually in order to specify the invention in more detail, if an imperative relationship is not expressly specified herein.

The invention thus alleviates the technical problems highlighted in conjunction with the prior art. In particular, an especially advantageous delivery unit for extracting liquid additive from a tank has been proposed, which delivery unit has a particularly advantageous fill level sensor. Furthermore, a particularly advantageous method for monitoring the fill level of the liquid additive in a tank has been specified. The invention is used, in particular, in the field of storing and delivering aqueous urea solution in a motor vehicle.

The invention claimed is:

1. A delivery unit configured to be mounted on a tank for extracting liquid additive from the tank, the delivery unit comprising:
   a housing having an outer side;
   a fill level sensor disposed at a wall of said housing, said sensor configured to measure a fill level of liquid additive in the tank, said fill level sensor configured to emit waves into an emission region of the tank permitting the fill level to be measured by using a propagation time measurement of the waves being reflected by a liquid surface and striking said fill level sensor again; and
   a calibration component mounted on said outer side of said housing, said calibration component having a spring portion, a bearing portion for being pressed against said wall by said spring portion for setting a longitudinal distance between said fill level sensor and at least one first reference surface disposed on said calibration component, extending at least partially into said emission region.

2. The delivery unit according to claim 1, which further comprises a second reference surface extending at least partially into said emission region and disposed at a second distance from said fill level sensor.

3. The delivery unit according to claim 1, wherein said fill level sensor is an ultrasound sensor.

4. The delivery unit according to claim 1, wherein said at least one first reference surface is configured to be positioned on said calibration component to define said first distance of said first reference surface from said fill level sensor.

5. The delivery unit according to claim 1, which further comprises a coupling layer, said housing having a wall, said fill level sensor being disposed in said housing and being in contact with said wall of said housing through said coupling layer, and said fill level sensor being configured to emit and receive waves through said wall.

6. The delivery unit according to claim 1, which further comprises a temperature sensor disposed on said fill level sensor and configured to measure a temperature of the liquid additive in said tank.

7. The delivery unit according to claim 6, wherein said housing has a protuberance, and said temperature sensor is disposed in said protuberance.

8. The delivery unit according to claim 1, wherein said at least one first reference surface is configured to permit at least one measurement of a propagation time of waves to said at least one first reference surface and back to said fill level sensor to additionally measure at least one property of the liquid additive.

9. A tank for storing liquid additive, the tank comprising:
   a tank base; and
   a delivery unit according to claim 1 disposed on said tank base.

10. A motor vehicle, comprising:
    an internal combustion engine;
    an exhaust-gas treatment device configured to purify exhaust gases of said internal combustion engine;
    a tank configured to store a liquid additive; and
    a delivery unit according to claim 1, said delivery unit configured to extract liquid additive from said tank and deliver the liquid additive into said exhaust-gas treatment device.

11. The delivery unit according to claim 1, further comprising a pump disposed in said housing.

12. The delivery unit according to claim 1, wherein said spring portion is disposed beyond said reference surface in a longitudinal direction of said calibration component.

13. The delivery unit according to claim 1, wherein said spring portion is provided in an upper region of said calibration component.

* * * * *